(12) United States Patent
Taguchi

(10) Patent No.: US 6,584,166 B2
(45) Date of Patent: Jun. 24, 2003

(54) X-RAY COMPUTERIZED TOMOGRAPHIC APPARATUS

(75) Inventor: Katsuyuki Taguchi, Nasu-gun (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 10/107,408

(22) Filed: Mar. 28, 2002

(65) Prior Publication Data

US 2002/0141531 A1 Oct. 3, 2002

(30) Foreign Application Priority Data

Apr. 3, 2001 (JP) ........................................ 2001-104915

(51) Int. Cl.⁷ ................................................ A61B 6/03
(52) U.S. Cl. ............................. 378/19; 378/8; 378/901
(58) Field of Search ................ 378/4, 8, 15, 19, 378/901

(56) References Cited

U.S. PATENT DOCUMENTS 5,598,453 A * 1/1997 Baba et al. ................. 378/146
5,825,842 A   10/1998 Taguchi ........................ 378/15
5,838,756 A   11/1998 Taguchi et al. ................. 378/4
6,084,936 A    7/2000 Patch ............................. 378/4
6,459,754 B1 * 10/2002 Besson et al. .................. 378/4

FOREIGN PATENT DOCUMENTS

JP       9-66051       3/1997

* cited by examiner

*Primary Examiner*—David V. Bruce
(74) *Attorney, Agent, or Firm*—Oblon, Spivak, McClelland, Maier & Neustadt, P.C.

(57) ABSTRACT

An X-ray computerized tomographic apparatus includes an X-ray tube device configured to irradiate an object to be examined with a pyramidal X-ray beam, a detector which has a plurality of detecting elements arrayed in a slice direction in which X-rays transmitted through the object are detected, a data extending unit which creates virtual data corresponding to an extension region located outside a region in which the detecting elements are arranged in the slice direction on the basis of real data detected by the detecting element, and a reconstructing unit which reconstructs image data on the basis of the real data and virtual data.

17 Claims, 9 Drawing Sheets

X-RAY COMPUTERIZED TOMOGRAPHIC APPARATUS

CROSS-REFERENCE TO RELATED APPLICATIONS

This application is based upon and claims the benefit of priority from the prior Japanese Patent Application No. 2001-104915, filed Apr. 3, 2001, the entire contents of which are incorporated herein by reference.

BACKGROUND OF THE INVENTION

1. Field of the Invention

The present invention relates to a so-called cone beam X-ray computerized tomographic apparatus which scans an object to be examined with a pyramidal X-ray beam to obtain 3-D information.

2. Description of the Related Art

In a cone beam scan scheme, an object to be examined is scanned with an X-ray beam emitted from an X-ray tube and trimmed into a pyramidal shape by an X-ray stop. The X-ray beam transmitted through the object is detected by a 2-D array type detector. As an X-ray detector of this type, a detector having an array of a relatively small number of line detectors, typically four line detectors, has become widespread. Recent years, however, have witnessed the advent of an X-ray detector having 32 or more arrays of line detectors by using solid-state detecting elements constituted by combinations of scintillator elements and photodiode elements or solid-state detecting elements made of selenium or the like which directly convert X-rays into electric charges. The 2-D array type detector has the form of the cylinder or the plane.

As a cone beam image reconstruction method, the Feld-Kamp method is generally used. The FeldKamp method is an approximate reconstruction method based on the fan beam convolution/back projection method. Convolution processing is performed by regarding data as a fan projection data on the premise that the cone angle is relatively small. However, back projection processing is performed along an actual ray.

That is, an image is reconstructed by the following procedure:

(1) assigning Z-axis-dependent weights to projection data;

(2) performing convolution for the data in (1) by using the same reconstruction function as that for a fan beam reconstruction; and (3) performing back projection with respect to the data in (2) along an actual oblique ray having a cone angle.

In such an image reconstruction method, however, the effective height of a field of view changes depending on the radius of the field of view. This problem will be described in detail below.

Figure 1:
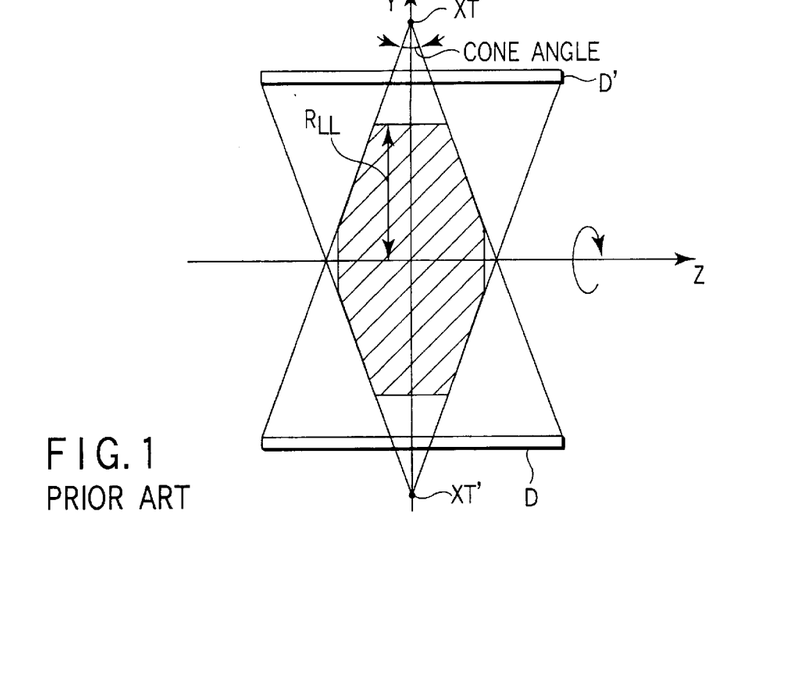
FIG. 1 is a side view showing a field of view whose radius is set to $R_{LL}$ in the prior art.
Figure 2:
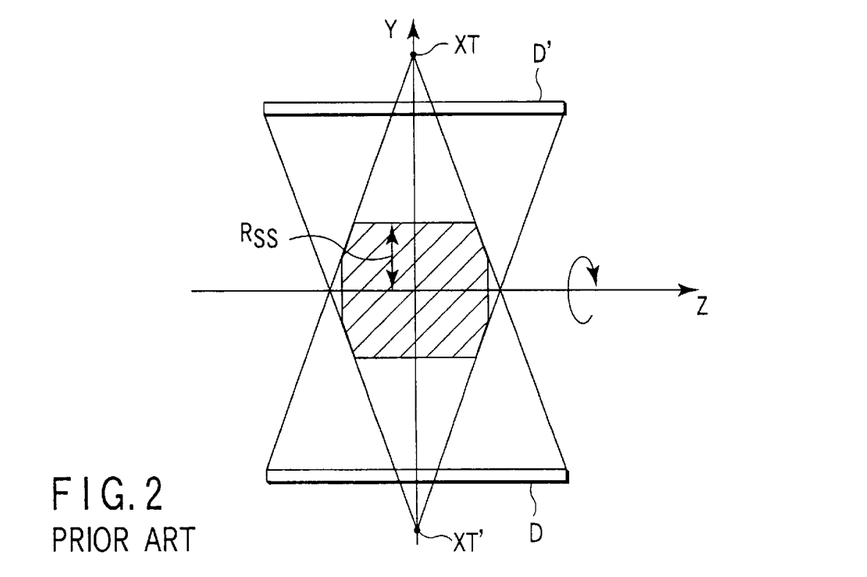
FIG. 2 is a side view showing the field of view whose radius is set to $R_{SS}$ in the prior art.

FIG. 1 is a side view of a field of view whose radius is set to a relatively long length $R_{LL}$. FIG. 2 is a side view of a field of view whose radius is set to a relatively short length $R_{SS}$. A radius R of the field of view is set to a length within which a region to be examined, e.g., the head, lungs, body. Note that the "effective height" of the field of view is defined by the length of the field of view in the slice direction in which the set radius R is maintained (the length of the field of view in the body axis direction of the object).

Figure 3A:
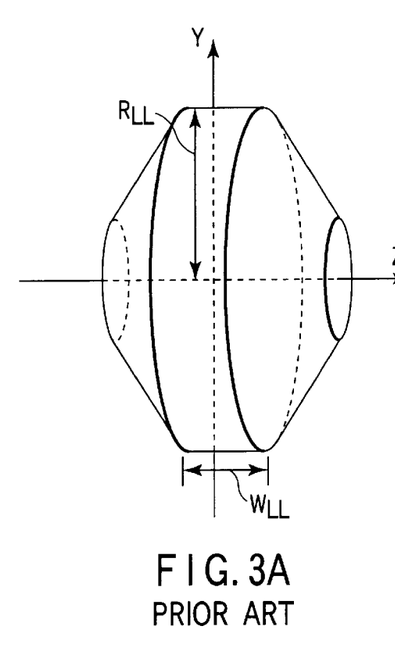
FIG. 3A is a view showing an effective height $W_{LL}$ of the field of view in FIG. 1 in the prior art.
Figure 3B:
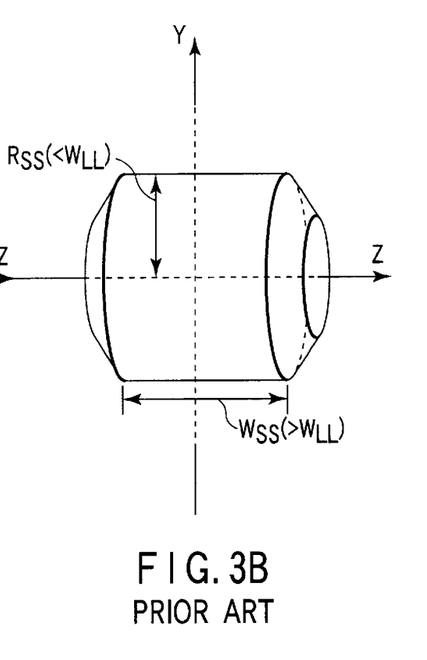
FIG. 3B is a view showing an effective height of the field of view in FIG. 2 in the prior art.

In the FeldKamp method, since data projected over one rotation are required, the maximum range in which image reconstruction can be done is limited to a cylindrical shape. In this range, the effective height of the field of view within which the radius R is maintained is limited to $W_{LL}$ when the radius is $R_{LL}$, as shown in FIG. 3A. When the radius is $R_{SS}$, the effective height is limited to $W_{SS}$, as shown in FIG. 3B. In this manner, the effective height of the field of view changes corresponding to the radius to which the field of view is set.

BRIEF SUMMARY OF THE INVENTION

It is an object of the present invention to reduce the dependence of an effective height on the radius of a field view in a cone beam type X-ray computerized tomographic apparatus.

According to the first aspect of the present invention, there is provided an X-ray computerized tomographic apparatus comprising an X-ray tube device configured to irradiate an object to be examined with a pyramidal X-ray beam, a detector which has a plurality of detecting elements arrayed in a slice direction in which X-rays transmitted through the object are detected, a data extending unit configured to create virtual data corresponding to an extension region located outside a region in which the detecting elements are arranged in the slice direction on the basis of real data detected by the detecting element, and a reconstructing unit configured to reconstruct image data on the basis of the real data and virtual data.

According to the second aspect of the present invention, there is provided An X-ray computerized tomographic apparatus comprising an X-ray tube device configured to irradiate an object to be examined with a pyramidal X-ray beam, a detector which has a plurality of detecting elements arrayed in a slice direction in which X-rays transmitted through the object are detected, an input device which inputs a radius of a field of view, and a reconstructing unit configured to reconstruct image data about a field of view in which the input radius is maintained within a predetermined length range in the slice direction on the basis of real data detected by the detecting element and virtual data created from the real data.

According to the third aspect of the present invention, there is provided an X-ray computerized tomographic apparatus comprising an X-ray tube device configured to irradiate an object to be examined with a pyramidal X-ray beam, a detector which has a plurality of detecting elements arrayed in a slice direction in which X-rays transmitted through the object are detected, and a reconstructing unit configured to reconstruct image data about a field of view having an arbitrary radius and fixed axis length on the basis of real data detected by the detecting element and virtual data created from the real data. Additional objects and advantages of the present invention will be set forth in the description which follows, and in part will be obvious from the description, or may be learned by practice of the present invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the present invention and, together with the general description given above and the detailed description of the embodiments given below, serve to explain the principles of the present invention.

FIG. 14 is a view showing another graphical user interface for setting reconstruction conditions, which is provided by the GUI controller in FIG. 4.

DETAILED DESCRIPTION OF THE INVENTION

An X-ray computerized tomographic apparatus according to a preferred embodiment of the present invention will be described below with reference to the views of the accompanying drawing. Note that X-ray computerized tomographic apparatuses include various types, e.g., a rotate/rotate-type that makes an X-ray tube and X-ray detector integrally rotate around an object to be examined, and a type that has many detecting elements fixed in the form of a ring-like array and makes only an X-ray tube rotate around an object to be examined, and the present invention can be applied to any of these types. The rotate/rotate-type will be exemplified here.

In order to reconstruct image data (tomographic image data), 360° projection data corresponding to one rotation around an object to be examined or (180°+fan angle) projection data in the half scan method is required. The present invention can be applied to either of these reconstruction schemes. The 360° method will be exemplified here.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor such as selenium by X-rays and movement of the electron-hole pairs to an electrode, i.e., a photoconductive phenomenon.

Recently, with advances toward the commercialization of a so-called multi-tube type X-ray CT apparatus having a plurality of pairs of X-ray tubes and X-ray detectors mounted on a rotating ring, related techniques have been developed. The present invention can be applied to both a conventional single-tube type X-ray CT apparatus and a multi-tube type X-ray CT apparatus. The single-tube type X-ray CT apparatus will be exemplified here.

Figure 4:
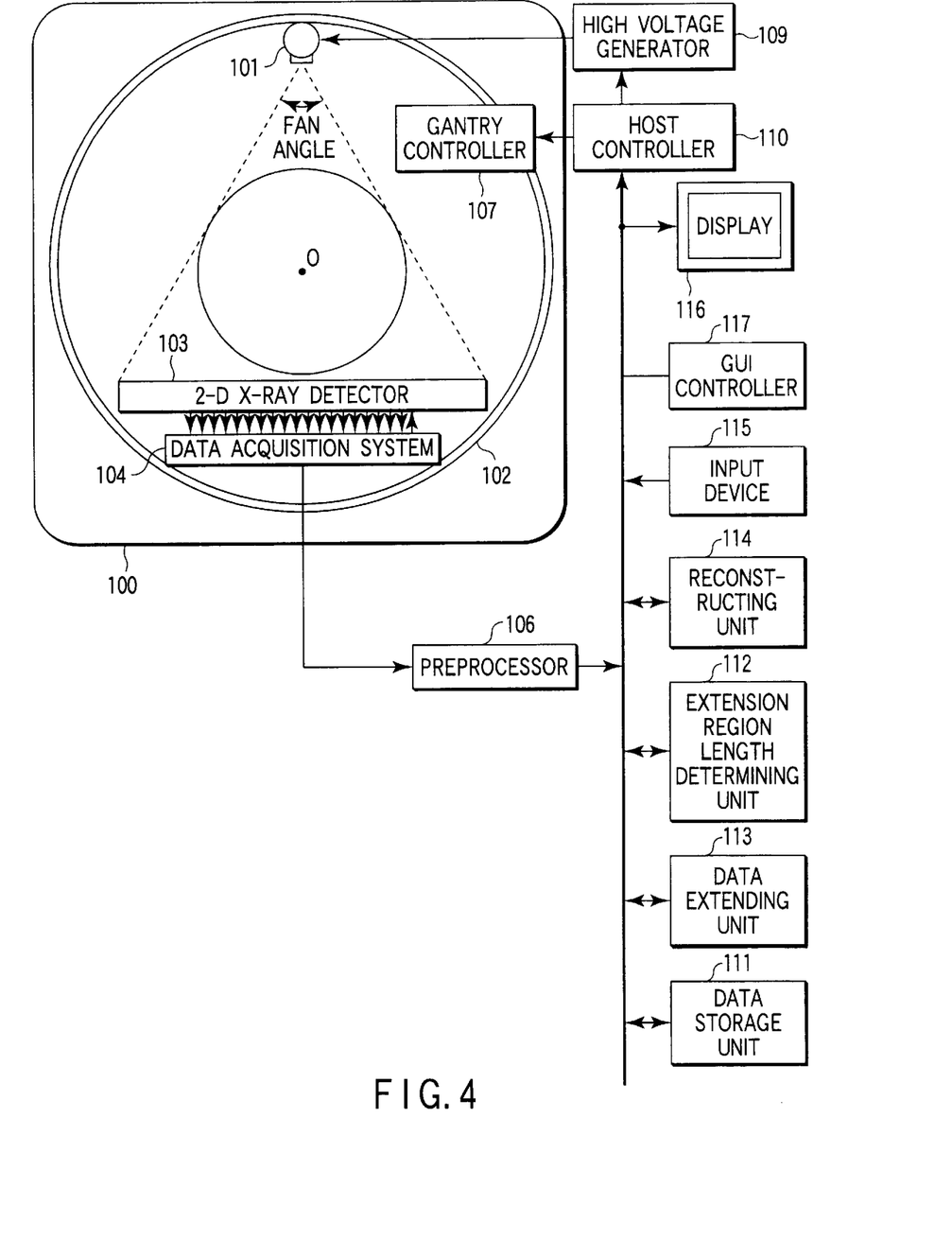
FIG. 4 is a view showing the arrangement of an X-ray computerized tomographic apparatus according to an embodiment of the present invention.

FIG. 4 is a view showing the arrangement of an X-ray computerized tomographic apparatus according to this embodiment. A gantry 100 houses a rotating ring 102 supported to be rotatable about a rotation axis O. An X-ray tube device 101 is mounted on the rotating ring 102. The X-ray tube device 101 has an X-ray tube and trimming device. The X-ray tube emits X-rays from its focal point upon application of a tube voltage from a high voltage generator 109 and supply of a tube current. The trimming device trims an X-ray beam from the X-ray tube into a rectangular shape. With this trimming, the X-ray beam is formed into a pyramidal shape.

Figure 5:
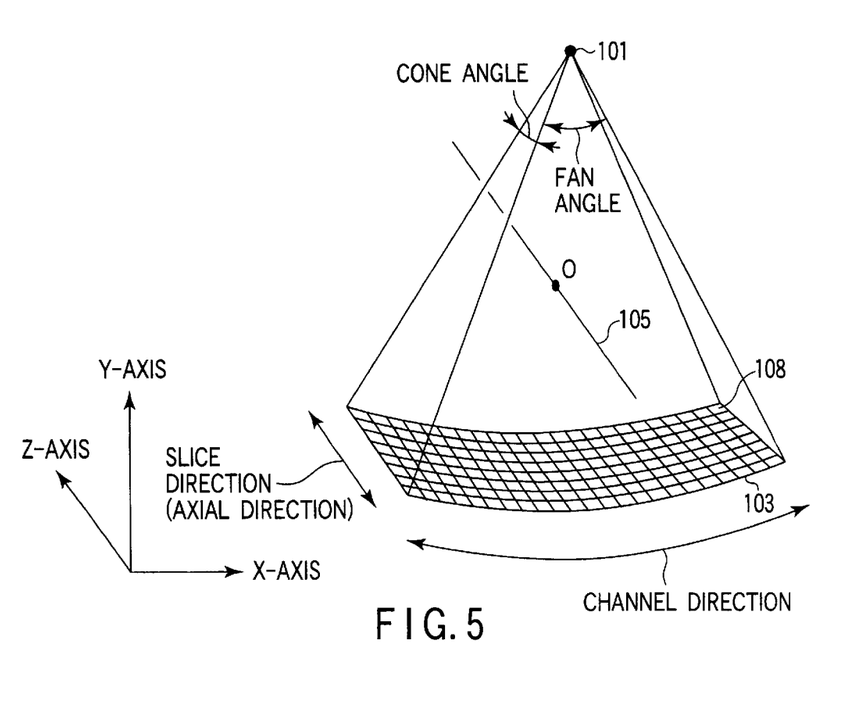
FIG. 5 is a perspective view showing a 2-D array type X-ray detector in FIG. 4.

A 2-D X-ray detector 103 is mounted on the rotating ring 102, together with the X-ray tube device 101. The 2-D X-ray detector 103 is mounted at a position and angle at which it squarely opposes the X-ray tube device 101 through the rotation axis O. As shown in FIG. 5, the 2-D X-ray detector 103 has a plurality of detecting elements 108. The plurality of detecting elements 108 are arranged two-dimensionally in two directions, i.e., a direction (slice direction) parallel to the rotation axis O and a direction (channel direction) which is perpendicular to the rotation axis O and gradually curves about an X-ray focal point. This 2-D X-ray detector 103 may be formed either by arranging, in the slice direction, a plurality of lines of detecting elements 108, each having detecting elements 108 arranged in a line in the channel direction, or by arranging a plurality of modules each formed by an M×N matrix of detecting elements 108.

In imaging operation, an object to be examined is placed between the X-ray tube device 101 and the 2-D X-ray detector 103. In helical scan, the relative positions of the object and gantry 100 are displaced at a predetermined speed.

A data acquisition system 104 generally called a DAS (Data Acquisition System) is connected to the output of the 2-D X-ray detector 103. The data acquisition system 104 has, for each channel, an I-V converter for converting the current signal obtained by each element of the 2-D X-ray detector 103 into a voltage, an integrator for periodically integrating these voltage signals in synchronism with an X-ray radiation period, an amplifier for amplifying an output signal from the integrator, and an analog/digital converter for converting an output signal from the amplifier into a digital signal.

The data (pure raw data) output from this data acquisition system 104 is transmitted to a preprocessor 106 through a slip ring or noncontact signal transmitter. The preprocessor 106 preprocesses this pure raw data. The preprocessing includes, for example, sensitivity disparity correction processing, processing of correcting an extreme decrease in an extreme decrease in signal intensity or signal omission due to an X-ray absorber, mainly a metal portion, and the like. The data (raw data) output from the preprocessor 106 is stored in a data storage unit 111 having a magnetic disk, magneto-optical disk, or semiconductor memory.

A GUI controller 117 displays a graphical user interface (GUI) on the screen of a display 116. The graphical user interface includes graphical elements such as icons, buttons, and pull-down menus which are brought into correspondence with a plurality of setting items such as scan conditions, reconstruction conditions, and the like. Various operations can be easily implemented by operating these graphical elements with a pointing device (input device) 115. Note that the reconstruction conditions include a size of a field of view for reconstructing to volume data. The size of a field of view is defined a radius R and a height W. Input operation for the size of the field of view, i.e. the radius R and the height W, is facilitated by a graphical element.

In order to fix the effective height of the field of view within which the radius R of the field of view set through the input device 115 is maintained is fixed to a predetermined length, an extension region length determining unit 112 determines a length by which the actual X-ray sensible region in which the detecting elements 108 of the 2-D X-ray detector 103 are arrayed is virtually extended outward in the slice direction on the basis of the radius R of the field of view set through the input device 115. Note that an extended virtual sensible region will be referred to as an extension region with respect to the actual sensible region.

The length of an extension region is computed on the basis of the radius R of the field of view. Alternatively, a table in which the different lengths of an extension region are respectively associated with different radii of the field of view may be created in advance and stored in the data storage unit 111, and the length of an extension region associated with the radius R of the field of view set through the input device 115 may be read out from the table.

Although described in detail later, the length of this extension region is so determined that the effective height W of the field of view within which the radius R set by the operator is maintained is kept constant regardless of the various radiuses R arbitrarily set.

A data extending unit 113 creates data (virtual data) on the basis of the raw data (real data) stored in the data storage unit 111. The virtual data correspond to a plurality of virtual detecting elements. The virtual detecting elements are virtually arrayed at the same density as that of the actual detecting elements in the extension region determined by the extension region length determining unit 112. Note that each ray is defined as a straight line drawn from the X-ray focal point of the X-ray tube device 101 to the center of a detecting element of the 2-D X-ray detector 103. Back projection processing is performed along this ray.

A reconstructing unit 114 reconstructs image data of the field of view having a cylindrical shape and the predetermined height W on the set radius R by the extended FeldKamp reconstruction method on the basis of real data within the range of 360° or 180°+fan angle of the X-ray tube device 101 and virtual data in the same range which is creased from the real data. The display 116 creates an arbitrary slice and 3-D rendering image on the basis of this image data and displays them.

Note that in back projection processing, strictly speaking, the reconstructing unit 114 performs back projection along a straight (calculated ray) connecting the X-ray focal point to the center of a voxel. In actuality, as described above, X-ray projection is performed along a ray (actual ray) connecting the X-ray focal point to the center of a detecting element. A slightest spatial deviation between the calculated ray and the actual ray causes a deterioration in image quality.

The reconstructing unit 114 performs deviation correction processing with respect to the real data and virtual data to reduce any deterioration in image quality by eliminating a slight spatial deviation between the mathematical ray and the actual ray. The deviation correction processing is described in detail in Jpn. Pat. Appln. KOKAI Publication No. 09-19425 and U.S. Pat. No. 5,825,842, and hence will be briefly described below. Consider back projection with respect to a given voxel. Assume that a point at which an extended straight light connecting the X-ray focal point to the center of the voxel intersects a plane of a sensible region is defined as a point C. Assume that the point C exists between the central points of the respective detecting elements at (n, m), (n, m+1), (n+1, m), and (n+1, m+1). The data of the point C is estimated from the data of a plurality of detecting elements near the point C, four detecting elements in this case, by distance interpolation. By performing back projection by using this estimated data, any deterioration in image quality due to the spatial deviation between the mathematical ray and the actual ray can be reduced.

Figure 6:
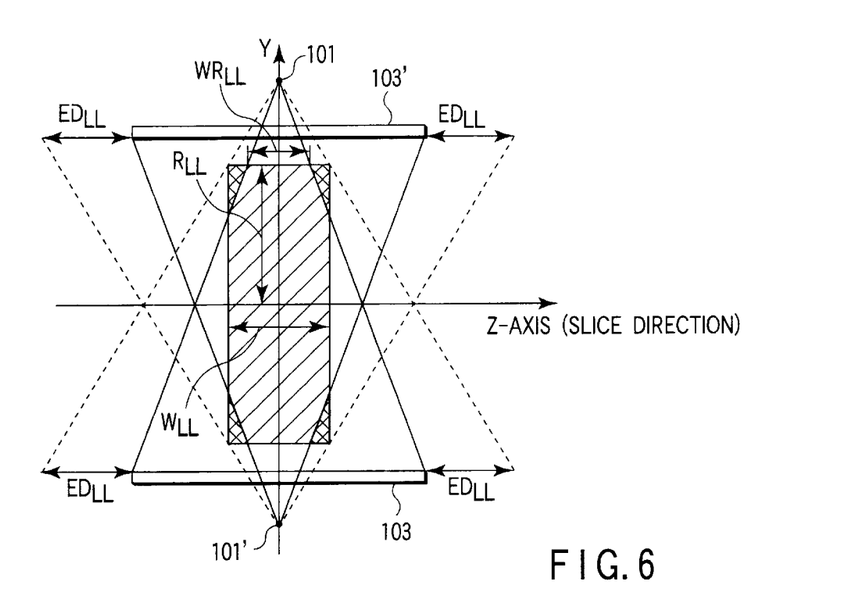
FIG. 6 is a view showing an extension width $ED_{LL}$ of an extension region determined by an extension region determining unit in FIG. 4 in accordance with a radius $R_{LL}$ of a field of view.
Figure 7:
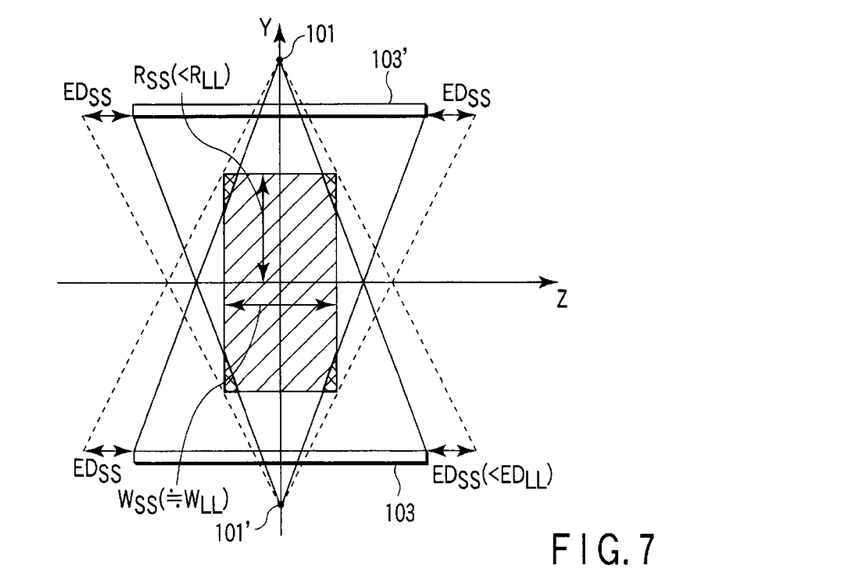
FIG. 7 is a view showing an extension width $ED_{SS}$ of an extension region determined by the extension region determining unit in FIG. 4 in accordance with the radius $R_{SS}$ of the field of view.
Figure 8A:
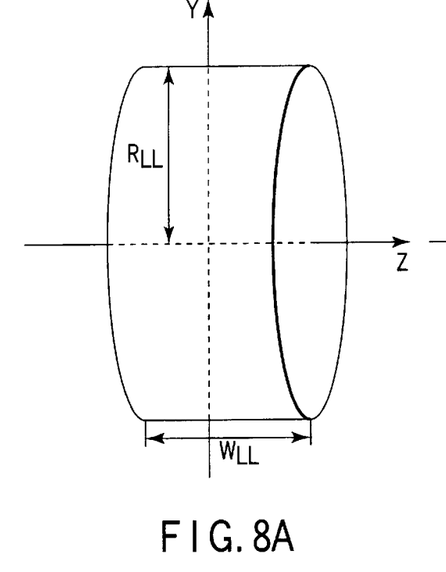
FIG. 8A is a view showing an effective height $W_{LL}$ of the field of view extended by the extension region in FIG. 6.
Figure 8B:
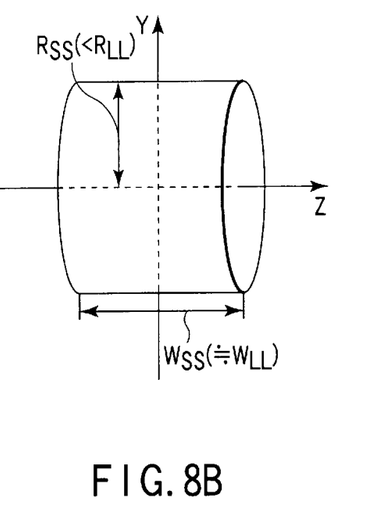
FIG. 8B is a view showing an effective height $W_{SS}$ of the field of view extended by the extension region in FIG. 7.

FIG. 6 shows a length (extension width) $ED_{LL}$ of an extension region which is determined by the extension region length determining unit 112 in accordance with a relatively large radius $R_{LL}$ of the field of view. FIG. 7 shows an extension width $ED_{SS}$ of an extension region which is determined by a relatively small radius $R_{SS}$. FIG. 8A shows the effective height $W_{LL}$ of the field of view which is determined in accordance with an extension width $ED_{LL}$ in FIG. 6. FIG. 8B shows the effective height $W_{SS}$ of the field of view which is determined in accordance with the extension width $ED_{SS}$. Referring to FIGS. 6 and 7, for the sake of easy understanding, an X-ray tube device and detector located at an angle position of 180° together with the X-ray tube device 101 and 2-D X-ray detector 103 located at an angle position of 0° are respectively denoted by 101' and 103'. In addition, referring to FIGS. 6 and 7, real data is indicated by the solid lines, and virtual data is indicated by the dashed lines. Furthermore, a region in the field of view which corresponds to real data is indicated by the hatching, whereas a region in the field of view which corresponds to virtual data is indicated by the mesh lines.

The purpose of creating virtual data is to reduce the dependence of the effective height W on the radius R. That is, even if the radius R of the field of view is variously set, the effective height W is fixed a predetermined length. To achieve this purpose, an extension region is added to the outside of an actual sensible region in the slice direction. In other words, the sensible region of the detector 113 is virtually extended in the slice direction, and the real data obtained by the outermost or neighboring detecting element is used as the virtual data of virtual elements on this extension region. Or virtual data is created from the real data obtained by the outermost detecting element and the real data obtained by a neighboring detecting element by extrapolation. In addition, the length of the extension region is changed in accordance with the set radius R such that the effective height is fixed to a predetermined length.

As shown in FIGS. 6 and 8A, when the radius R of the field of view is set to the relatively long radius $R_{LL}$, the length of the extension region is determined as $ED_{LL}$. The effective height of the field of view is determined as $W_{LL}$ by the extension width $ED_{LL}$. Obviously, the effective height $W_{LL}$ of the field of view is longer than the effective height $WR_{LL}$ determined depending on the actual sensible region of the detector 103 under the condition of the same radius $R_{LL}$.

As shown in FIGS. 7 and 8B, when the radius R of the field of view is set to the relatively short radius $R_{SS}$, the length of the extension region is determined as $ED_{SS}$. The effective height $W_{SS}$ of the field of view is determined by the extension width $ED_{SS}$.

The length $ED_{LL}$ of the extension region is determined to be longer than the length $ED_{SS}$ of the extension region. The respective lengths are geometrically determined on the basis of the shortest distance from the X-ray focal point of the X-ray tube device 101 to the detection surface of the 2-D X-ray detector 103, the radius R of the field of view, the effective height W of the field of view, and the length of the actual sensible region of the 2-D X-ray detector 103 such that the effective heights W of the final fields of view FOV become equal or almost equal to each other, i.e., the effective heights W of the final fields of view FOV are fixed to a predetermined length or almost fixed to the predetermined length.

Since the extension region is set outside the actual sensible region of the detector 103, no virtual data on the extension region is actually measured. Therefore, such data must be created. Two methods that balance the creation efficiency and image quality deterioration suppression are provided. Either of the methods may be used. Alternatively, the two methods may be implemented to be selectively used in accordance with a user's instruction, or two types of images may be reconstructed by using the two methods to allow the user to finally select one of them.

Figure 9:
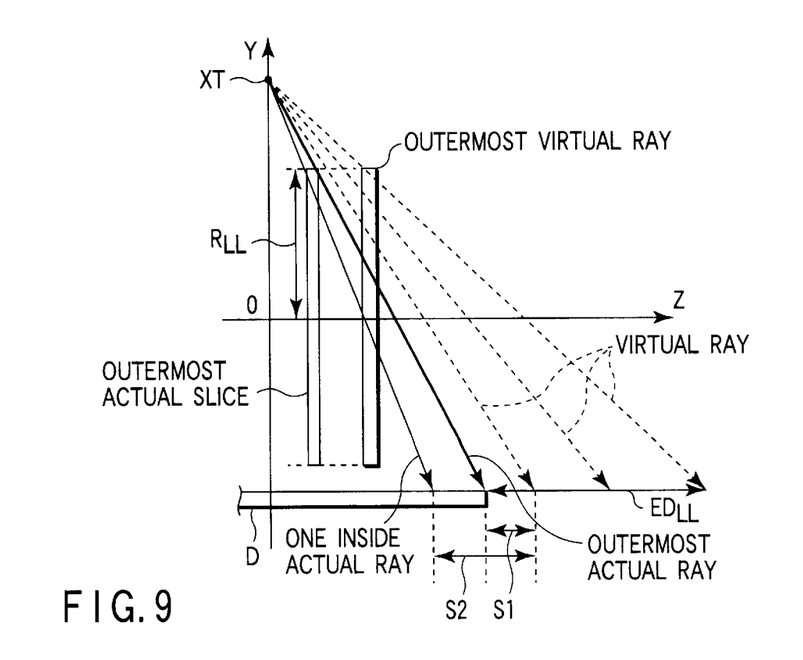
FIG. 9 is a view showing virtual rays on the extension region in FIG. 6.
Figure 10:
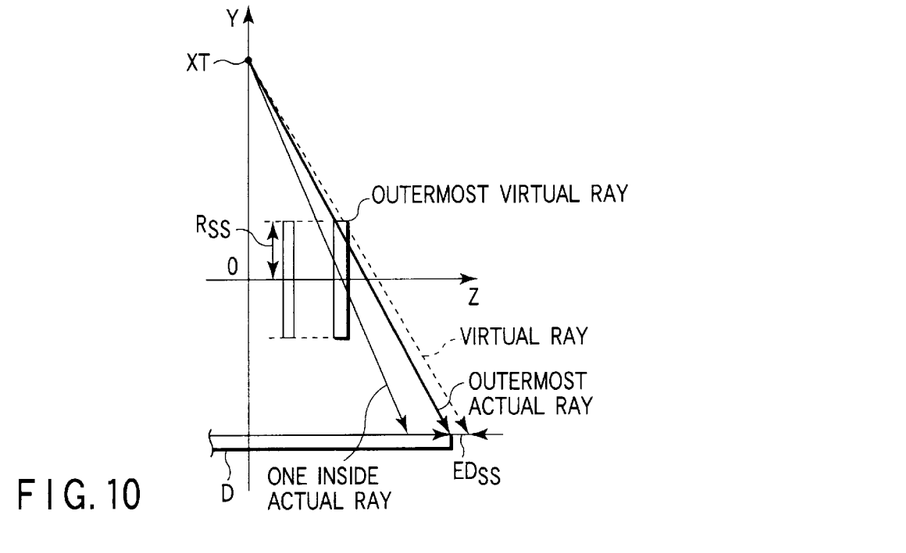
FIG. 10 is a view showing a virtual ray on the extension region in FIG. 7.

According to one of the methods, as shown in FIGS. 9 and 10, the real data which is on the same line as that of the virtual data obtained by a virtual detecting element in the slice direction and is detected by an actual detecting element nearest to the virtual detecting element, i.e., the real data detected by one of the actual detecting elements which is located at the outermost position in the slice direction, is used as virtual data without any change.

In practice, this method can be realized by read control on data from the data storage unit 111 to the reconstructing unit 114. More specifically, in creating virtual data, the data extending unit 113 accesses the data storage unit 111 with the same address as that of the real data detected by the detecting element located at the outermost position, and the real data detected by the detecting element located at the outermost position is read as the virtual data detected by the corresponding virtual detecting element to the reconstructing unit 114.

In this method, the virtual data detected by a plurality of virtual detecting elements arranged in the slice direction on the extension region are replaced by the same real data. In practice, such virtual data influence the peripheral portion of the slice which are indicted by the hatching in FIGS. 6 and 7. In actual examination, a region of interest is often located near the center of a slice, and less importance is attached to the peripheral portions of the slice than to the portion near its center. When a region of interest is placed near the center of a slice, peripheral portions of the slice are often relatively simple tissue structures from the anatomical point of view. For this reason, a deterioration in the image quality of the peripheral portions does not pose any serious problem.

Instead of assigning data on the detecting element in line of the extreme outside, one data of the inside detecting element in line may be assigned in the virtual data.

According to the other method, virtual data is created from the real data detected by a plurality of actual detecting elements located near the corresponding virtual detecting element by extrapolation. More specifically, as shown in FIGS. 9 and 10, virtual data is calculated from real data d1 detected by the actual detecting element located nearest to the virtual detecting element for the virtual data, i.e., at the outermost position, and real data d2 detected by the actual detecting element located nearest to the outermost actual detecting element on the basis of distances S1 and S2 between the respective actual detecting elements and the virtual detecting element on the detection surface. Obviously, interpolation may be performed by using the real data detected by three or more neighboring actual detecting elements including the outermost detecting element. Although this method is slightly improved as compared with the preceding method, image quality (image reproducibility and reliability in this case) still slightly deteriorates. It is, however, assumed that this deterioration strongly influences peripheral portions of a slice, and a deterioration in the image quality of such peripheral portions poses no serious problem. The average data of detecting element in several lines may be assigned in the virtual data.

The dependence of the effective height W on the radius R of the field of view is eliminated or reduced by setting an extension region outside the actual sensible region of the detector 103 in the slice direction, creating projection data in this extension region from real data, and changing the height W of the extension region in accordance with the radius R of the field of view in this manner.

Figure 11:
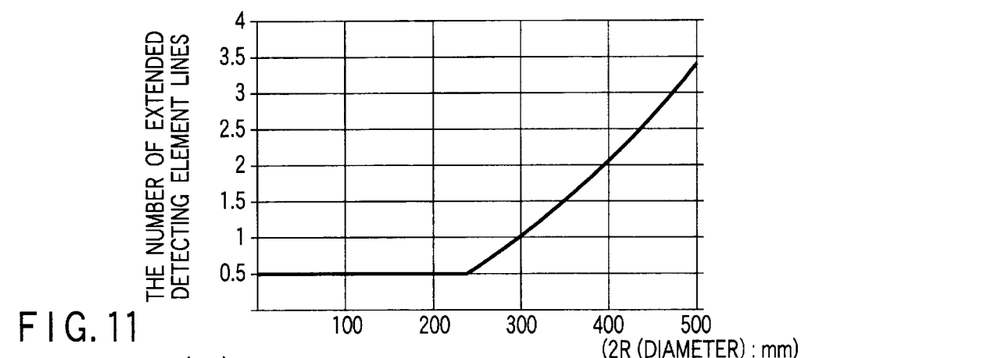
FIG. 11 is a table stored in a data storage device in FIG. 4, which shows extension widths (the numbers of detecting element lines) in correspondence with the radii of the field of view.

FIG. 11 shows the result obtained by simulating the relationship between the radius R of the field of view and a length ED of an extension region. Referring to FIG. 11, the length ED of the extension region is expressed as the number of virtual extended detecting element lines. When a diameter 2R of the field of view is about 250 mm or less, almost no extension region needs to be set. This is because the predetermined effective height W can be attained by real data alone. When the diameter 2R of the field of view exceeds about 250 mm, an extension region is set to suppress a decrease in the effective height W of the field of view. The extension width ED of the extension region is increased almost in proportion to an increase in the radius R of the field of view.

Figure 12:
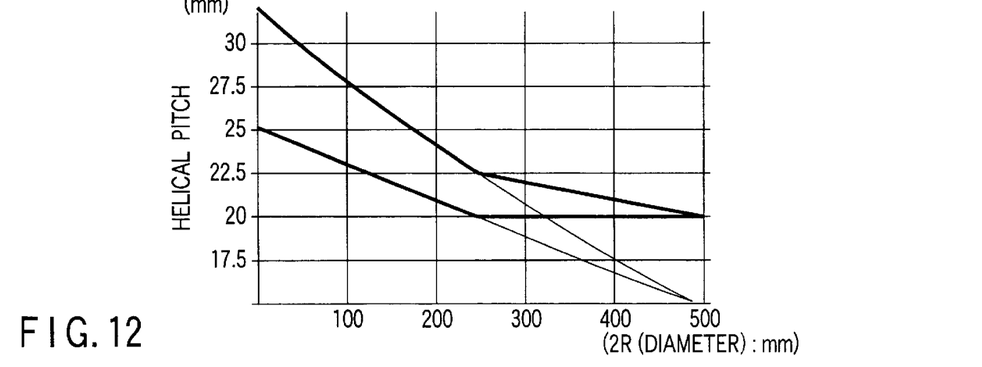
FIG. 12 is a table stored in the data storage device in FIG. 4, which shows helical pitches in correspondence with the radii of the field of view.

In helical scan, in order to suppress variations in the effective height of the field of view with the radius R of the field of view, the unit distance by which the top of the bed moves per rotation, i.e., the helical pitch, must be changed. As shown with thick line in FIG. 12, variations in helical pitch can be suppressed by using this method.

Figure 13:
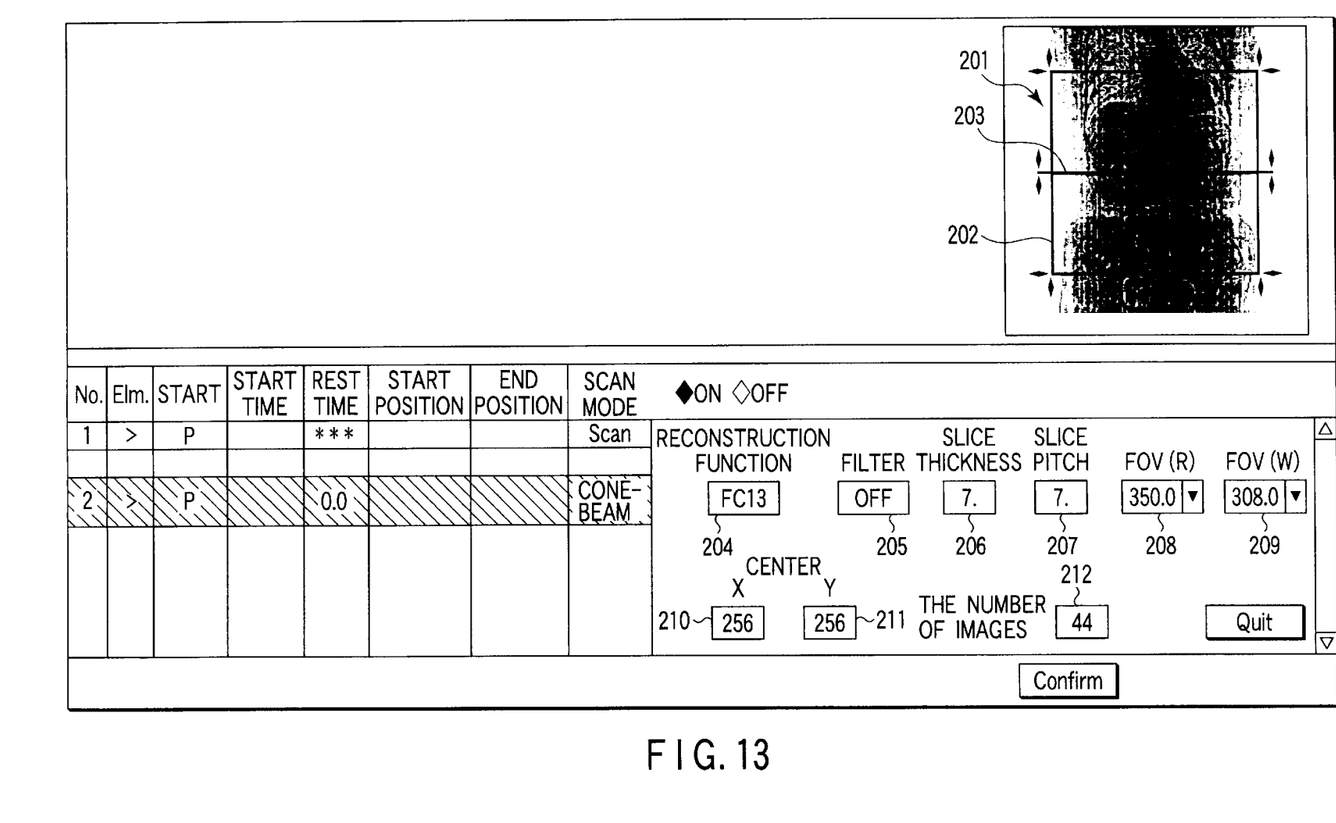
FIG. 13 is a view showing a graphical user interface for setting reconstruction conditions, which is provided by a GUI controller in FIG. 4.

FIG. 13 shows a graphical user interface (GUI) for setting reconstruction conditions which is displayed on the screen of the display 116 by the GUI controller 117. This GUI displays reconstruction condition items, together with a scanogram 201. On the scanogram 201, the field of view is represented by a rectangular pattern 202. The length of this rectangular cursor 202 (in the vertical direction on the drawing) corresponds to the effective width W of the field of view, and the width of the rectangular pattern 202 (in the horizontal direction on the drawing) corresponds to the diameter 2R of the field of view. In addition, a central line 203 of the field of view is displayed on the scanogram 201.

Setting buttons 204 to 212 for a reconstruction function, filter, slice thickness, slice pitch, the radius R of the field of view, the effective width W of the field of view, the central position (X, Y) of the field of view, and the number of images are arranged below the scanogram 201. The slice pitch represents the distance between the central lines of adjacent slices. The number of images is automatically set in accordance with this slice pitch, slice thickness, and the effective width W of the field of view. When a numerical value is input to the button 208 corresponding to the radius R of the field of view, the width of the rectangular pattern 202 changes accordingly. In contrast to this, when the width of the rectangular pattern 202 is changed while dragging the pointer, the numerical value in the output data management section 208 corresponding to the radius R of the field of view changes accordingly. Likewise, the effective width W of the field of view changes in association with the length of the rectangular pattern 202. In addition, the central position (X, Y) of the field of view changes in association with the position of the rectangular pattern 202 and central line 203 as well.

The radius R and effective width W of the field of view are input by the following method in addition to the input methods of inputting numerical values and expanding/contracting the rectangular pattern 202. As shown in FIG. 14, an input method of selectively designating a region to be examined from pull-down menus 213 and 214 listing regions to be examined, e.g., the head, lungs, and body, is prepared for supporting input operation. The standard values of the radius R and weighted average of the field of view are associated with the respective regions to be examined, e.g., the head, lungs, and body. The GUI controller 117 automatically sets the radius R and effective width W of the field of view to the standard values associated with a selected region to be examined.

Figure 15:
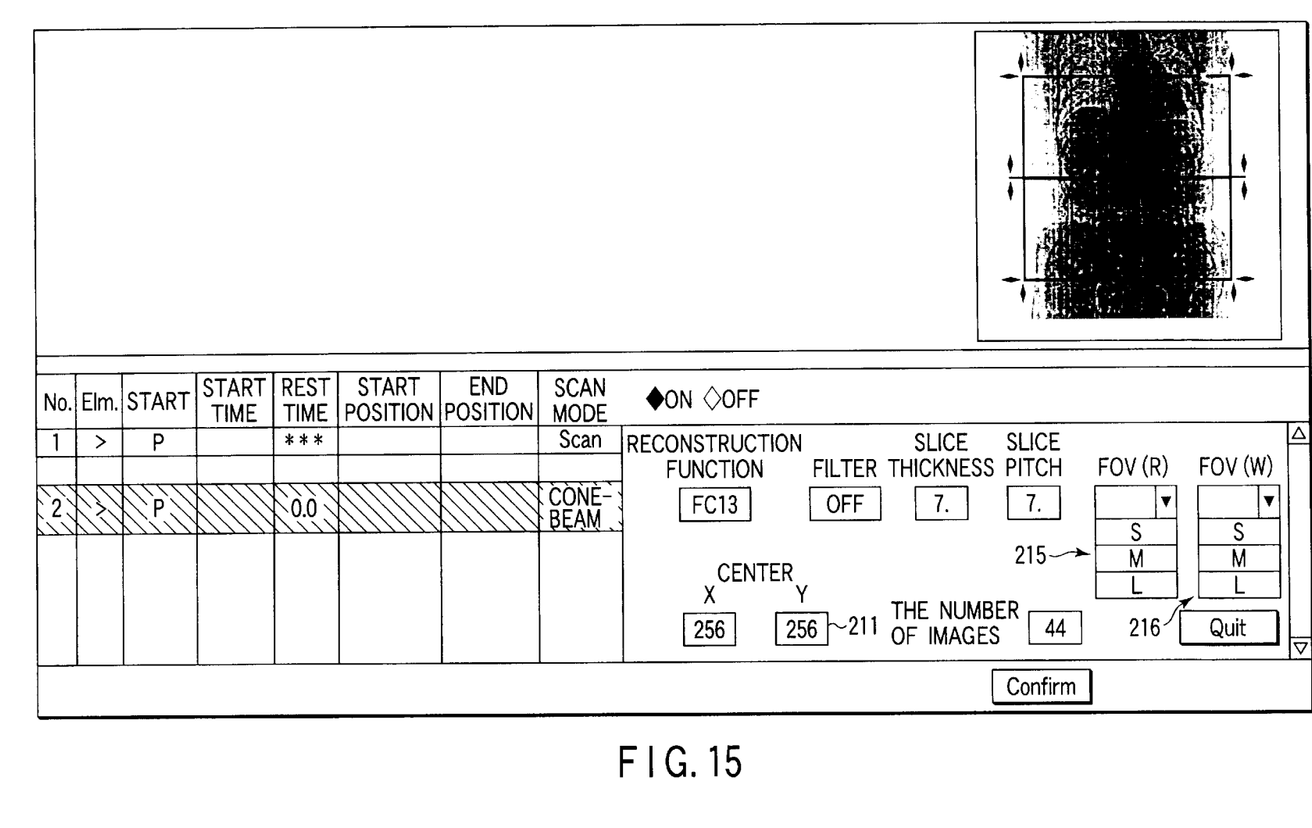
FIG. 15 is a view showing still another graphical user interface for setting reconstruction conditions, which is provided by a GUI controller in FIG. 4.

Note that the method of displaying the choices of the pull-down menus 213 and 214 is not limited to the method using the names of regions to be examined, and the choices may be expressed in sizes like S (small), M (medium), and L (large), as shown in FIG. 15.

The present invention is not limited to the above embodiment, and various changes and modifications of the embodiment can be made in the execution stage within the spirit and scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computerized tomographic apparatus comprising:
   an X-ray tube device configured to irradiate an object to be examined with a pyramidal X-ray beam;
   a detector which has a plurality of detecting elements arrayed in a slice direction in which X-rays transmitted through the object are detected;
   a data extending unit configured to create virtual data corresponding to an extension region located outside a region in which the detecting elements are arranged in the slice direction on the basis of real data detected by the detecting element; and
   a reconstructing unit configured to reconstruct image data on the basis of the real data and virtual data.

2. An apparatus according to claim 1, wherein said data extending unit uses real data detected by one of the plurality of detecting elements which is located at an outermost position as the virtual data.

3. An apparatus according to claim 1, wherein said data extending unit creates the virtual data on the basis of real data detected by one of the plurality of detecting elements which is located at an outermost position and real data detected by at least one detecting element adjacent to the detecting element located at the outermost position.

4. An apparatus according to claim 3, wherein said data extending unit creates the virtual data from the real data detected by the detecting element located at the outermost position and the real data detected by the adjacent detecting element by extrapolation.

5. An apparatus according to claim 1, wherein said data extending unit creates the virtual data on the basis of real data detected by one of the plurality of detecting elements which is located at an outermost position and real data detected by the detecting element immediately adjacent to the detecting element located at the outermost position.

6. An apparatus according to claim 5, wherein said data extending unit creates the virtual data from the real data detected by the detecting element located at the outermost position and the real data detected by the immediately adjacent detecting element by extrapolation.

7. An apparatus according to claim 1, further comprising:
   an input device which inputs a radius of the field of view; and
   an extension region determining unit configured to determine a length of the extension region on the basis of the input radius of the field of view.

8. An apparatus according to claim 7, wherein said extension region length determining unit determines a length of the extension region to set an effective height of the field of view, within which the input radius of the field of view is maintained, to a predetermined length.

9. An apparatus according to claim 8, further comprising a storage device which stores a table in which different lengths of the extension region correspond with different radii associated with the field of view.

10. An apparatus according to claim 7, further comprising a GUI controller configured to provide a graphic user interface including choices associated with a plurality of regions to be examined so as to support inputting of a diameter of the field of view.

11. An apparatus according to claim 7, further comprising a GUI controller configured to provide a graphic user interface including choices associated with different sizes so as to support inputting of a diameter of the field of view.

12. An X-ray computerized tomographic apparatus comprising:
   an X-ray tube device configured to irradiate an object to be examined with a pyramidal X-ray beam;
   a detector which has a plurality of detecting elements arrayed in a slice direction in which X-rays transmitted through the object are detected;
   an input device which inputs a radius of a field of view; and
   a reconstructing unit configured to reconstruct image data about a field of view in which the input radius is maintained within a predetermined length range in the slice direction on the basis of real data detected by the detecting element and virtual data created from the real data.

13. An apparatus according to claim 12, further comprising a GUI controller configured to provide a graphic user interface including choices associated with a plurality of regions to be examined so as to support inputting of a diameter of the field of view.

14. An apparatus according to claim 12, further comprising a GUI controller configured to provide a graphic user interface including choices associated with different sizes so as to support inputting of a diameter of the field of view.

15. An X-ray computerized tomographic apparatus comprising:
- an X-ray tube device configured to irradiate an object to be examined with a pyramidal X-ray beam;
- a detector which has a plurality of detecting elements arrayed in a slice direction in which X-rays transmitted through the object are detected; and
- a reconstructing unit configured to reconstruct image data about a field of view having an arbitrary radius and fixed axis length on the basis of real data detected by the detecting element and virtual data created from the real data.

16. An apparatus according to claim 15, wherein the virtual data corresponds to an extension region outside the region in which the detecting elements are arrayed.

17. An X-ray computerized tomographic apparatus comprising:
- an X-ray tube device configured to irradiate an object to be examined with a pyramidal X-ray beam;
- a detector which has a plurality of detecting elements arrayed in a slice direction in which X-rays transmitted through the object are detected;
- an input device which inputs a size of a field of view; and
- a reconstructing unit configured to reconstruct image data about a field of view in which the input size is maintained within a predetermined length range in the slice direction on the basis of real data detected by the detecting element and virtual data created from the real data.

* * * * *